(12) United States Patent
Siff et al.

(10) Patent No.: US 11,633,594 B2
(45) Date of Patent: Apr. 25, 2023

(54) ELECTROTHERAPY AND NEUROSTIMULATION MEDICAL DEVICE APPARATUS AND METHOD

(71) Applicant: BioWave Corporation, Norwalk, CT (US)

(72) Inventors: Bradford Siff, Norwalk, CT (US); John Carter, Belle Harbor, NY (US)

(73) Assignee: BioWave Corporation, Norwalk, CT (US)

( * ) Notice: Subject to any disclaimer, the term of this patent is extended or adjusted under 35 U.S.C. 154(b) by 777 days.

(21) Appl. No.: 16/661,728

(22) Filed: Oct. 23, 2019

(65) Prior Publication Data

US 2020/0121925 A1    Apr. 23, 2020

Related U.S. Application Data

(60) Provisional application No. 62/749,233, filed on Oct. 23, 2018.

(51) Int. Cl.
*A61N 1/36* (2006.01)

(52) U.S. Cl.
CPC ..... *A61N 1/36021* (2013.01); *A61N 1/36031* (2017.08); *A61N 1/36034* (2017.08)

(58) Field of Classification Search
CPC .......................... A61N 1/36021; A61N 1/36031
USPC .......................................................... 607/46
See application file for complete search history.

(56) References Cited

U.S. PATENT DOCUMENTS

| 6,584,358 | B2 | 6/2003 | Carter et al. |
| 6,760,627 | B2 | 7/2004 | Carter et al. |
| 6,792,315 | B2 | 9/2004 | Carter et al. |
| 6,853,863 | B2 | 2/2005 | Carter et al. |
| 7,013,179 | B2 | 3/2006 | Carter et al. |

(Continued)

OTHER PUBLICATIONS

U.S. Appl. No. 60/175,003.

*Primary Examiner* — Nadia A Mahmood
(74) *Attorney, Agent, or Firm* — Duane Morris LLP

(57) ABSTRACT

A method and apparatus are disclosed for providing therapeutic electric current to a treatment site of a patient. The steps of the method comprise generating a first and second signal having a frequency difference between 1 Hz and 300 Hz, wherein each signal has a frequency of at least 1 KHz and are amplified by Class D switching amplifiers, minimizing the DC component of the first and second signals using balanced amplifiers; operatively coupling a first electrode of at least one pair of electrodes to a patient's body on or beneath a first epidermal or mucous membrane surface; operatively coupling a second electrode of at least one pair of electrodes to a patient's body on or beneath a second epidermal or mucous membrane surface; forming a therapeutic signal configured to reduce pain at a treatment site by simultaneously sending a first signal from the first electrode to the second electrode and sending a second signal from a second electrode to the first electrode, and then simultaneously sending the first signal from the second electrode back to the first electrode and the second signal from the first electrode back to the second electrode, wherein the first and second signals are linearly independent off phase alternating current signals; and adjusting the therapeutic signal utilizing a feedback system based on impedance changes within the patient's body.

20 Claims, 9 Drawing Sheets

(56) References Cited

U.S. PATENT DOCUMENTS

| | | |
|---|---|---|
| 7,130,696 B2 | 10/2006 | Carter et al. |
| 2005/0033381 A1* | 2/2005 | Carter .................... A61N 1/326 607/69 |
| 2005/0187591 A1 | 8/2005 | Carter et al. |
| 2007/0016268 A1 | 1/2007 | Carter et al. |
| 2008/0033492 A1 | 2/2008 | Siff et al. |

* cited by examiner

ELECTROTHERAPY AND NEUROSTIMULATION MEDICAL DEVICE APPARATUS AND METHOD

CROSS-REFERENCE TO RELATED APPLICATION

This application claims priority to U.S. Provisional Patent Application Ser. No. 62/749,233 filed Oct. 23, 2019, the entirety of which is incorporated herein by reference.

FIELD

The present disclosure generally relates to the technical field of pain treatment. More specifically, the present disclosure is directed to an electro-therapy method and apparatus for relieving pain arising from temporary or chronic conditions in the body.

DESCRIPTION OF THE RELATED ART

Traditionally, electrotherapy devices have generated alternating current frequencies using a variety of different methods. For example, Matthews' U.S. Pat. No. 5,269,304 issued on Dec. 14, 1993 discloses an electrotherapy apparatus that includes at least two electrodes adapted to feed oscillating current to selected sites on or beneath the epidermal or mucous surface remote from the treatment site. The Matthews' patent uses a common return electrode provided at the treatment site that is subjected to the sum of the currents from the two feed electrodes. The feed electrodes may be contact feed electrodes or capacitive feed electrodes. The feed electrodes may operate at different frequencies so that the treatment site is stimulated by the beat frequency. This may be about 80 or 130 Hz, if an anaesthetizing effect is required.

Traditional devices, like the above described Matthews' patent, have undesirable effects and deficiencies that the present disclosure solves. Another electrotherapy device, Carter, et al. U.S. Pat. No. 6,584,358 issued on Jun. 24, 2003 discloses an electro-therapy apparatus and method for providing therapeutic electric current to a treatment site of a patient, having means for providing two oscillating or pulsing electric alternating currents, of frequencies which differ from each other by as little as 1 Hz and up to about 250 Hz, but each being of frequency at least about 1 KHz. The apparatus and method requires only one feed electrode adapted to feed the electric currents to selected feed sites on or beneath the epidermal or mucous surface of the patient, and only one return electrode adapted to be positioned on or beneath the epidermal or mucous surface of the patient, locally to the treatment site.

This device, described in the Carter, et al. patent is undesirable because of the heat generated that results from the use of a class A/B amplifier, the large heat sink requirement, the need for ventilation holes and as a result, the inability to meet quality standards for home healthcare medical devices.

Embodiments of the present disclosure provide for a smaller portable unit. More specifically, the present disclosure controls and manages the output of a digital high frequency alternating current to deliver electrical signals to a dynamic load. Embodiments of the present disclosure advantageously provide for a smaller more efficient electrotherapy device. Additionally, the present disclosure provides for an electrotherapy device that has water resistant properties allowing for more portability. Finally, embodiments of the present disclosure improve efficiency of the electrical operations negating the need for a heat sink.

SUMMARY

In some embodiments of the present disclosure, a method is disclosed for providing therapeutic electric current to a treatment site of a patient. The steps of the method comprise generating a first and second signal having a frequency difference between 1 Hz and 300 Hz, wherein each signal has a frequency of at least 1 KHz and are amplified by Class D switching amplifiers, minimizing the DC component of the first and second signals using balanced amplifiers; operatively coupling a first electrode of at least one pair of electrodes to a patient's body on or beneath a first epidermal or mucous membrane surface; operatively coupling a second electrode of at least one pair of electrodes to a patient's body on or beneath a second epidermal or mucous membrane surface; forming a therapeutic signal configured to reduce pain at a treatment site by simultaneously sending a first signal from the first electrode to the second electrode and sending a second signal from a second electrode to the first electrode, and then simultaneously sending the first signal from the second electrode back to the first electrode and the second signal from the first electrode back to the second electrode, wherein the first and second signals are linearly independent off phase alternating current signals; and adjusting the therapeutic signal utilizing a feedback system based on impedance changes within the patient's body.

In various embodiments of the present disclosure, a method is disclosed for providing therapeutic electric current to a treatment site of a patient. The steps of the method comprise generating a first and second signal having a frequency difference between 1 Hz and 300 Hz, wherein the first and second signal are two sinusoidal alternating current signals having a base frequency value of between 200 Hz and 500 KHz which are amplified by Class D switching amplifiers; coupling a first electrode of at least one pair of electrodes to a patient's body on or beneath a first epidermal or mucous membrane surface; coupling a second electrode of at least one pair of electrodes to a patient's body on or beneath a second epidermal or mucous membrane surface; and forming a therapeutic signal configured to reduce pain at a treatment site by simultaneously sending a first signal from the first electrode to the second electrode and sending a second signal from a second electrode to the first electrode, and then simultaneously sending the first signal from the second electrode back to the first electrode and the second signal from the first electrode back to the second electrode, wherein the first and second signals are linearly independent off phase alternating current signals.

In some embodiments of the present disclosure, an electro therapy and neurostimulation device is provided including a substantially rectangular shape having at least one corner of the outer peripheral edge of the device at an angle, and a depression disposed within the angled portion of the device and a female port disposed within the depression configured to receive a male connector. Wherein the depression comprises a plurality of indentations configured to receive a cable attached to the male connector such that the cable is located against the side edges of the substantially rectangular device when the male connector is inserted into the female port.

BRIEF DESCRIPTION OF DRAWINGS

Various aspects of the present disclosure will be or become apparent to one with skill in the art by reference to the following detailed description when considered in connection with the accompanying exemplary non-limiting embodiments.

DETAILED DESCRIPTION

Figure 1:
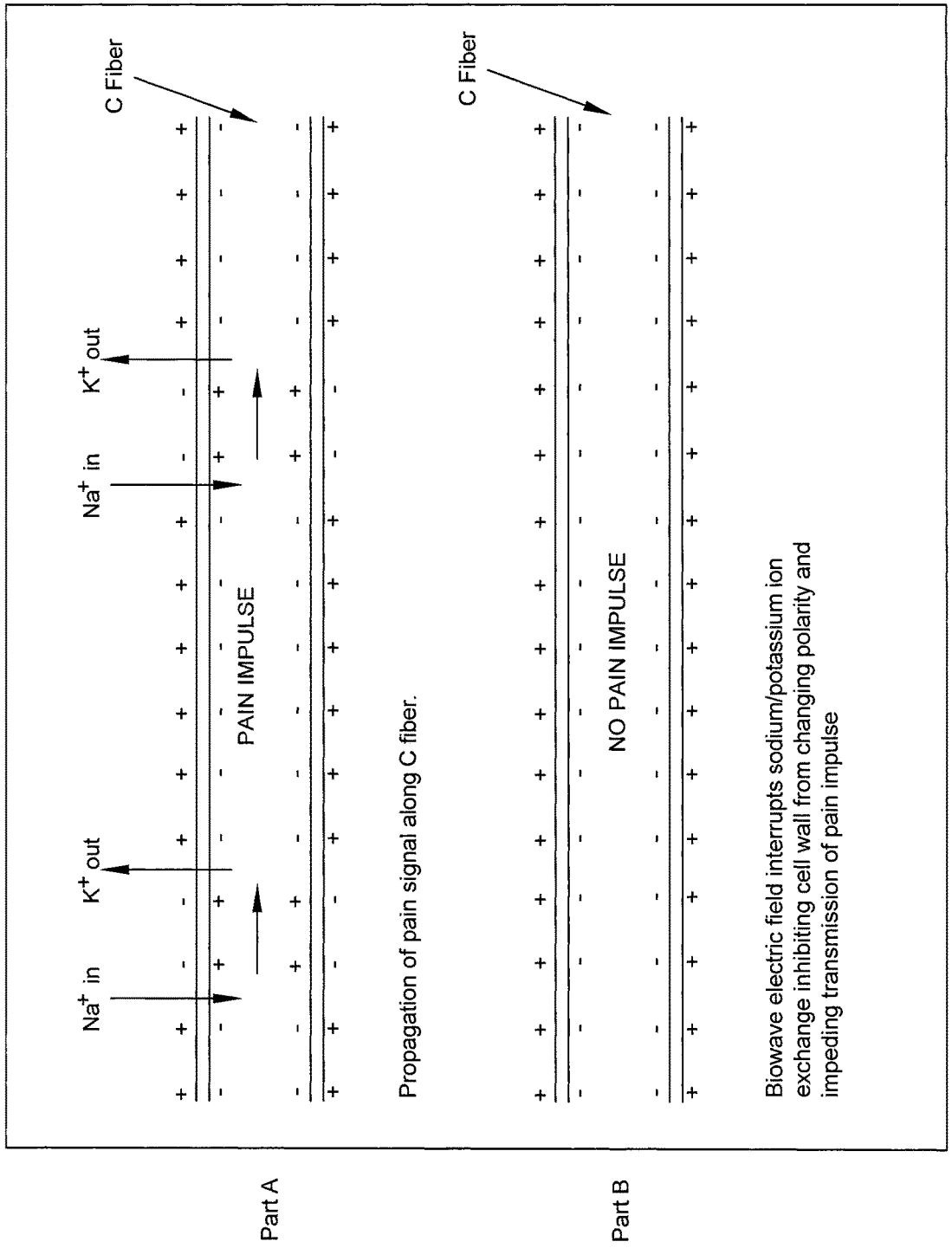
FIG. 1 illustrates the hyperpolarization mechanism of pain reduction in accordance with some embodiments of the present disclosure.

With reference to the figures, where like elements have been given like numerical designations to facilitate an understanding of the drawings, various embodiments of an apparatus for a multi-purpose handheld tool are described. The figures are not drawn to scale The following description is provided as an enabling teaching of a representative set of examples. Many changes can be made to the embodiments described herein while still obtaining beneficial results. Some of the desired benefits discussed below can be obtained by selecting some of the features discussed herein without utilizing other features. Accordingly, many modifications and adaptations, as well as subsets of the features described herein are possible and can even be desirable in certain circumstances. Thus, the following description is provided as illustrative and is not limiting.

This description of illustrative embodiments is intended to be read in connection with the accompanying drawings, which are to be considered part of the entire written description. The drawing figures are not necessarily to scale and certain features of the invention can be shown exaggerated in scale or in somewhat schematic form in the interest of clarity and conciseness. In the description of embodiments disclosed herein, any reference to direction or orientation is merely intended for convenience of description and is not intended in any way to limit the scope of the present disclosure. Relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral," and the like are to be interpreted relative to one another or relative to an axis of elongation, or an axis or center of rotation, as appropriate. Terms concerning attachments, coupling, and the like, such as "connected" "interconnected," "attached," and "affixed," refer to a relationship wherein structures are secured or attached to one another either directly or indirectly through intervening structures, as well as both movable or rigid attachments or relationships, unless expressly described otherwise. The terms "operatively connected" or "operatively coupled" are such an attachment, coupling or connection that allows the pertinent structures to operate as intended by virtue of that relationship. The term "adjacent" as used herein to describe the relationship between structures/components includes both direct contact between the respective structures/components referenced and the presence of other intervening structures/components between respective structures/components.

As used herein, use of a singular article such as "a," "an" and "the" is not intended to exclude pluralities of the article's object unless the context clearly and unambiguously dictates otherwise.

In various embodiments, a differentially-applied frequency-separated electrotherapy apparatus and method is disclosed for providing therapeutic electric current to a treatment site of a patient. The apparatus and method include having at least two individually generated and amplified oscillating or pulsing alternating currents, of frequencies which differ from each other by as a little as 1 Hz and up to about 300 Hz, wherein the base frequency value of the two frequencies can be between 200 Hz and 500 KHz. The apparatus and method require at least two electrodes adapted to act as pain site and return electrodes which provide electric current beneath the epidermal or mucous surface of the patient, directly over or next to the source of pain.

In some embodiments, the method of electrotherapy includes providing two individually generated and amplified signals with a frequency difference between them which is applied to one or more pairs of electrodes placed on the body directly over locations of pain and/or over the origin of the pain. According to various embodiments, as will be described in further detail below, since the signals share a common power supply return path, each signal's electrode acts as the return path for the opposing signal. Advantageously, the signals non-linearly mix on polarizable weakly rectifying structures along the current path to evoke a neuro-stimulated pain signal transmission blocking effect by interfering with nerve impulse signal transmission.

In various embodiments, at least one pair of electrodes are placed directly over locations of pain, on or beneath the epidermal or muscular surface of a patient coupled to a generator feeding via the at least one pair of electrodes with two or more oscillating or complex morphology electric currents to a patient. In some embodiments, the respective selected electrode placement locations are opposite one another on the patient's body with a pain site located on a line vector in between the electrodes with the line vector perpendicular to each skin surface on which the electrodes reside. In various embodiments, as described below, the at least one pair of electrodes may be placed directly over a single location of pain. In some embodiments, the currents generated by the at least one pair of electrodes are a frequency of at least about 1 KHz and have a current difference between each electrode respectively as little as 1 Hz by up to about 300 Hz. As described in part above, a non-linear action of nerve fiber membranes causes a multiplication of the two independent high frequency signals in a volume of tissue surrounding and beneath each of the at least two electrodes to produce a therapeutic effect in the hemisphere surrounding and beneath each of the at least two electrodes. The multiplication yields a distribution of synthesized sum and difference frequencies among which is a therapeutic low frequency signal that is equivalent to a beat frequency of the signals.

A described in part above, two high frequency electronic wave-forms are introduced into the body non-invasively through at least one pair of disposable electrodes placed on the skin directly over the pain site, according to some embodiments. In various embodiments, for two locations of pain, each electrode is placed directly over a painful area. In some embodiments, for one location of pain, one electrode is placed directly over a single location of pain, the second electrode may be placed over a bony area which is a comfortable location to receive stimulation.

The Feed Signals are exponentially multiplied by materials within the body giving rise to a low frequency component, the beat frequency, in the form of an electric field within the volume of tissue the shape of a hemisphere beneath as well as surrounding the electrode, the size of which is defined by the geometry of the electrode. The size and shape of the volume of tissue affected can be changed and is dependent upon electrode placement, geometry and materials, as well as the amplitude of the Feed Signals.

Physiological Application

FIG. 1 illustrates the hyperpolarization mechanism of pain reduction according to various embodiments. Pain signals from receptors that are large enough to exceed the trigger threshold for the exchange of sodium and potassium ions across a nerve cell membrane do so through changes in the ion permeability of this membrane. This ion exchange causes a polarity change across and along the cell wall of the nerve fiber affecting the transmission of pain information along certain C type fibers as shown in Part A of FIG. 1. Several mechanisms of action caused by the Beat Frequency to reduce pain, namely (1) Frequency Conduction Block (also called Hyperpolarization), (2) Gate Control, (3) increased blood flow and (4) the release of endorphins or other opiate-like analogs.

Frequency Conduction Block. In Part B of FIG. 1, with the low frequency electric field in place, the membranes of C fibers that fall within the electric field are hyperpolarized. As a result, the sodium/potassium ion exchange is inhibited and the cell wall is prevented from changing polarity (from a negative potential to a positive potential) thus impeding the transmission of action potentials. As a result, pain impulses along the C fibers are blocked—similar in action to local chemical anesthesia, except without any deleterious side effects.

A further explanation of the therapeutic Hyperpolarization mechanism is that the resulting beat frequency, its signal morphology and current densities within the volume of tissue around and below each electrode, causes an alteration in the nerve cell membrane's sodium/potassium ion concentrations or ion exchange kinetics. As a result, the charge polarity of the nerve cell wall is prevented from changing and is therefore unable to transmit pain impulses.

Empirically, the difference signal does affect the sensory fibers, as some loss of proprioception at the skin as well as induction of hypoesthesia in the region of the active low frequency electrical field occurs about 5 minutes into the treatment, similarly to but not as absolute as a chemical anesthetic. Following a 30-minute treatment, hypoesthesia remains typically for up to 20 minutes post treatment.

Empirically, the difference signal also affects muscle tissue, which is polarized, in that it holds muscle tissue in tension during the treatment, which results in the patient feeling a deep, smooth sensation from the electrical field which is comfortable and provides for excellent patient compliance using the device.

Figure 2:
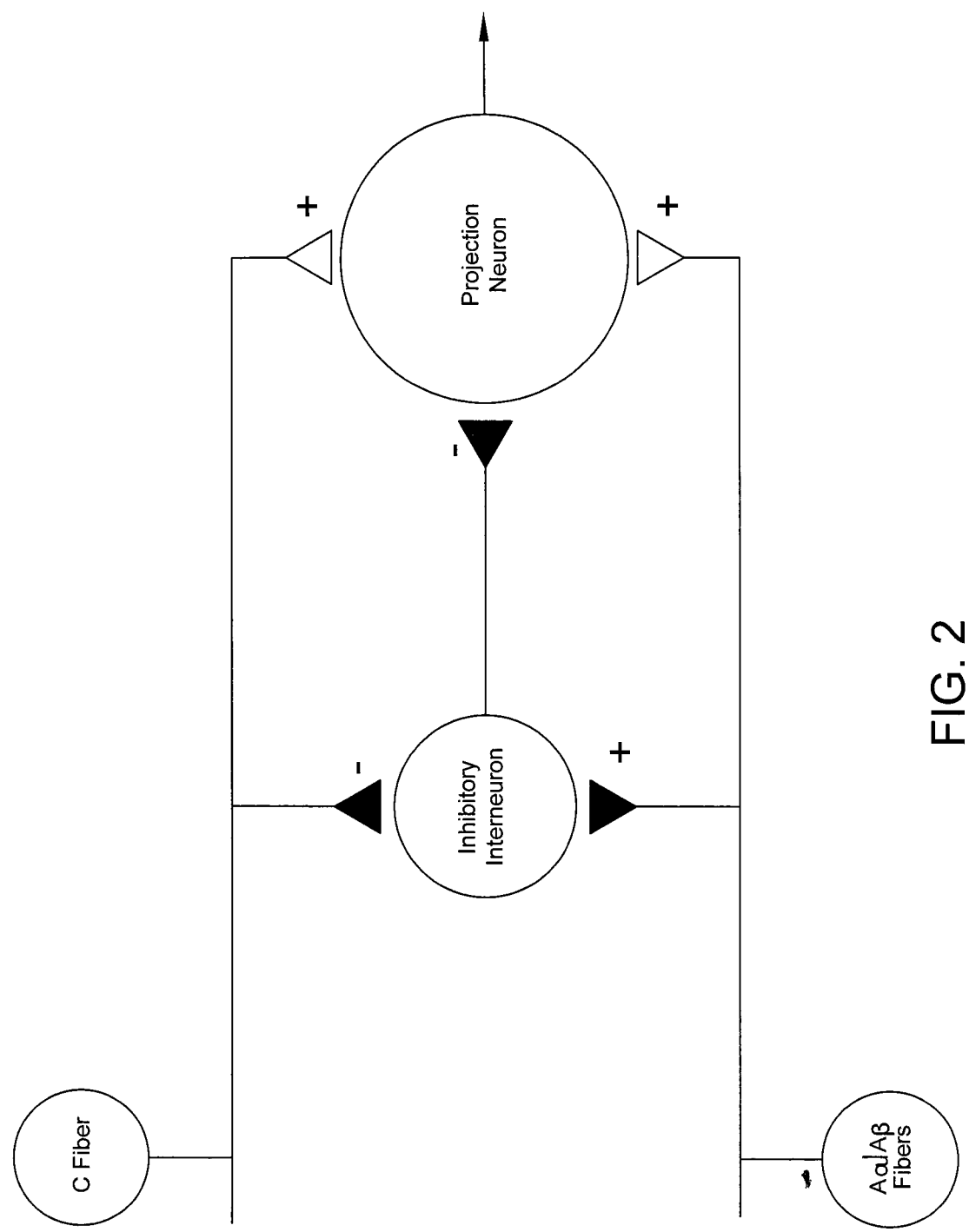
FIG. 2 illustrates the gate control mechanism of pain reduction in accordance with some embodiments of the present disclosure.

Gate Control. Gate Control focuses on interactions of four classes of neurons in the dorsal horn of the spinal cord as shown in FIG. 2: (1) C fibers which are unmyelinated, (2) $A\beta/A\delta$ fibers which are myelinated, (3) projection neurons whose activity results in the transmission of pain information, and (4) inhibitory interneurons which inhibit the projection neuron, thus reducing the transmission of pain information.

The projection neuron is directly activated by both $A\beta/A\delta$ and C fibers. However, only the $A\beta/A\delta$ fibers activate the inhibitory interneuron. Thus when $A\beta/A\delta$ fibers are stimulated by the beat frequency from the electric field, the inhibitory interneuron is activated and prevents the projection neuron from transmitting pain information to the brain. The C fiber is left in a state analogous to an open electrical circuit so that transmission of the sensation of pain is suppressed.

Increased Blood Flow. An additional mechanism of action is that the resulting low frequency electrical field that forms beneath and surrounding both electrodes can accelerate any charged species under its influence. This may lead to an increase in local blood flow. Medical studies have shown that proper blood flow is required for the healing of any wound or injury. With the treatment application of the apparatus, there appears to be a concomitant increase in blood flow in the volume of tissue where the electric field is present that accelerates healing. Clinical evidence shows there is also a concomitant increase in range of motion and reduction of stiffness for up to 24 hours following the treatment.

Release of Endorphins or Other Opiate-like Analogs. Empirical evidence suggests that residual pain relief and an increase in range of motion can last for up to 24 hours following a thirty (30) minute treatment. The residual effect involves either a refractory mechanism involving the membrane itself or the local release of endorphins, enkaphlins or other opiate-like analogs.

Unique Control and Management Apparatus and Method

According to various embodiments of the present disclosure, the electro therapy device controls the output of a handheld high frequency neurostimulator for providing a therapeutic treatment inside the body to treat pain and other conditions by utilizing a digital amplifier, feedback control utilizing filters, and other circuitry to provide comfortable treatment to patients. Advantageously, the electrotherapy device described in the present disclosure eliminates electrical spikes and jolts regardless if the patient is siting or moving about during the treatment.

One embodiment of the electrotherapeutic apparatus involves two signals: S1 represents a first signal at a first frequency and S2 represents a second signal at a second frequency. S1 and S2 are linearly independent AC signals. At any given instant one electrode can act as the source of the signal while the other electrode can serve as its return. Due to the AC nature of the signal these roles become reversed as a function of the instantaneous polarity of said signal. The time dependent roles of the electrode vary for the two signals as they are not in phase. It will be appreciated that the effect within the body from the combination of S1 and S2 passing through the body to the respective electrodes produces the pain-relieving effects described above.

Figure 3:
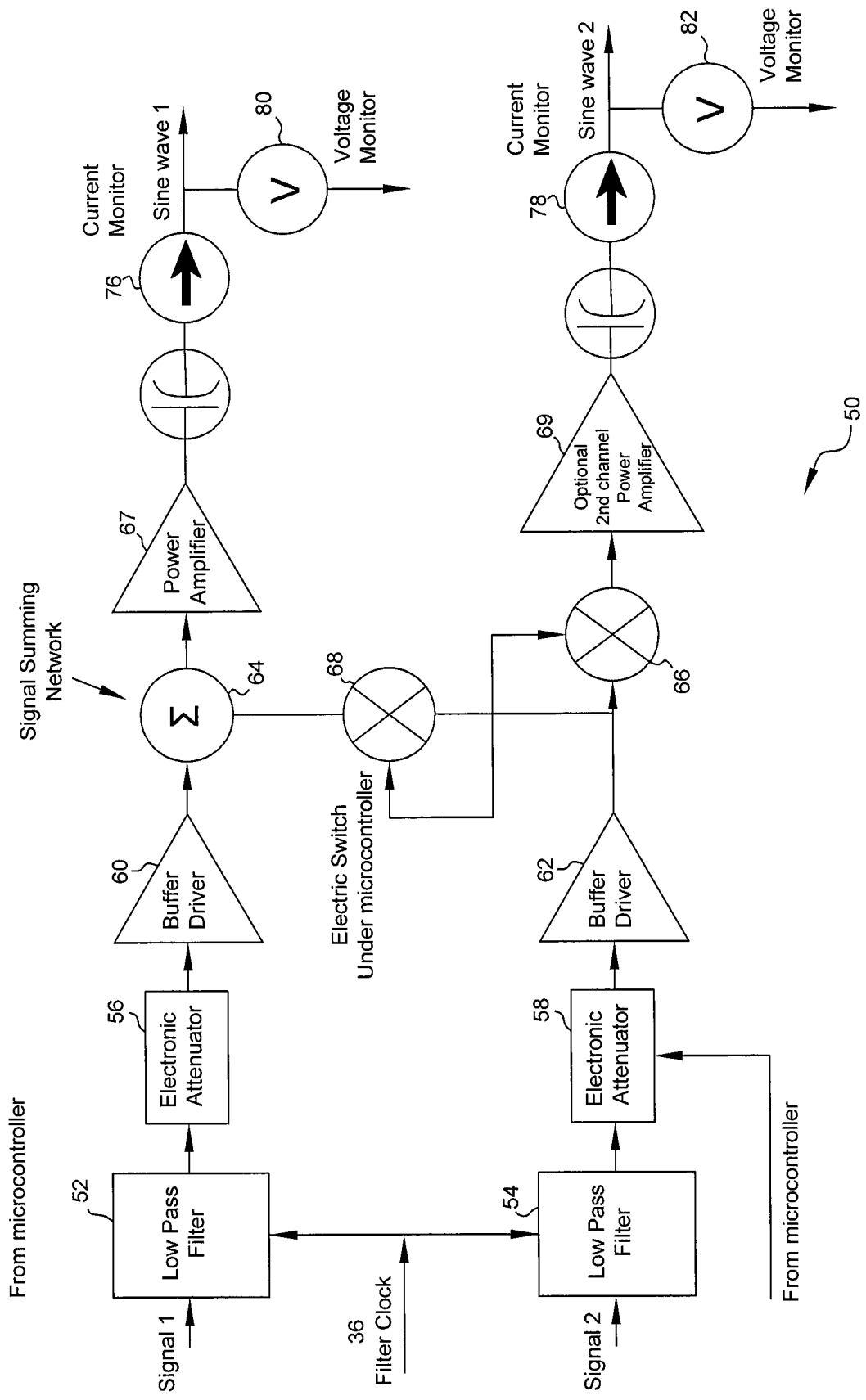
FIG. 3 illustrates output portions of an electrotherapeutic device in accordance with some embodiments of the present disclosure.

FIG. 3 illustrates output portions of an electrotherapeutic device in accordance with some embodiments of the present disclosure. More specifically, FIG. 3 depicts a sub-system 50 for converting Signal 1 and Signal 2 to sine wave signals. As discussed above, the ultimate output signals of the electrotherapy device need to be as close to a pure sine wave as possible. Signal 1 and Signal 2 are initially logic level square-type waves. These signals are limited to 0.6V amplitude by the transistor limiters. The outputs of these limiters are applied independently to high-order low pass filters 52 and 54. The filter clock 36, if switched capacitor filters are used, output is coupled to each of the filters. These filters suppress the higher order harmonics present in the limited square waves leaving low distortion sine waves at the reference frequencies. These sinusoidal signals are amplified and applied to electronic attenuators or programmable amplifiers 56 and 58 (under microprocessor 12 control) to control the level of the signal applied to the power amp stage, discussed below, and ultimately to the patient. The signals are then buffered 60 and 62 and applied to a power gain stage. The power stage consists of one or more amplifiers 67,69 capable of supplying a wide range of voltages into any physiological and electrode load over the frequency ranges used. Depending on the desired level of system integration and/or portability required, this amplifier stage can be either of the linear Classes A or $AB_1$ or the nonlinear switching Class D type. In various embodiments, use of the Class D amplifier, as discussed in further detail below, provides the efficiency and in turn, minimal heat generation properties, to allow enclosure of the therapeutic device for water resistant properties.

For Class D amplifiers a high-speed comparator varies the pulse width of a switching power transistor (MOSFET type). This modulation is called pulse width modulation and is driven by the original signal's frequency, amplitude and desired gain. The sampling of the reference signal, derived from either a PLL reference or DDS, is sampled at a rate at several orders of magnitude higher than the highest frequency component in said reference. The output of the power transistor is low-pass filtered by a passive LC network to yield the amplified signal. The mode of amplifier operation is particularly attractive since power conversion efficiencies of over 90% can be obtained as opposed to the efficiencies of linear amplifiers which are between 40% to 70%. The microcontroller 12 sets, via electronic switching 68, whether the signals are summed at an amplifier to create the mixed signal or applied individually to the power stage and thereby allows the mixing to take place within the patient's body. Additionally, one or more channels and/or return signal paths can be multiplexed with electronic power switching during zero crossing of the sine wave signals (via processor control). This multiplexing or switching allows multiple electrodes to be fed from the amplifiers or connected to an analog return. This is done to synthesize a larger effective target region on or within the patient. The patient is electrically isolated from leakage to power mains by the isolated plastic housing of the Apparatus and by the use of a battery power supply.

Figure 4:
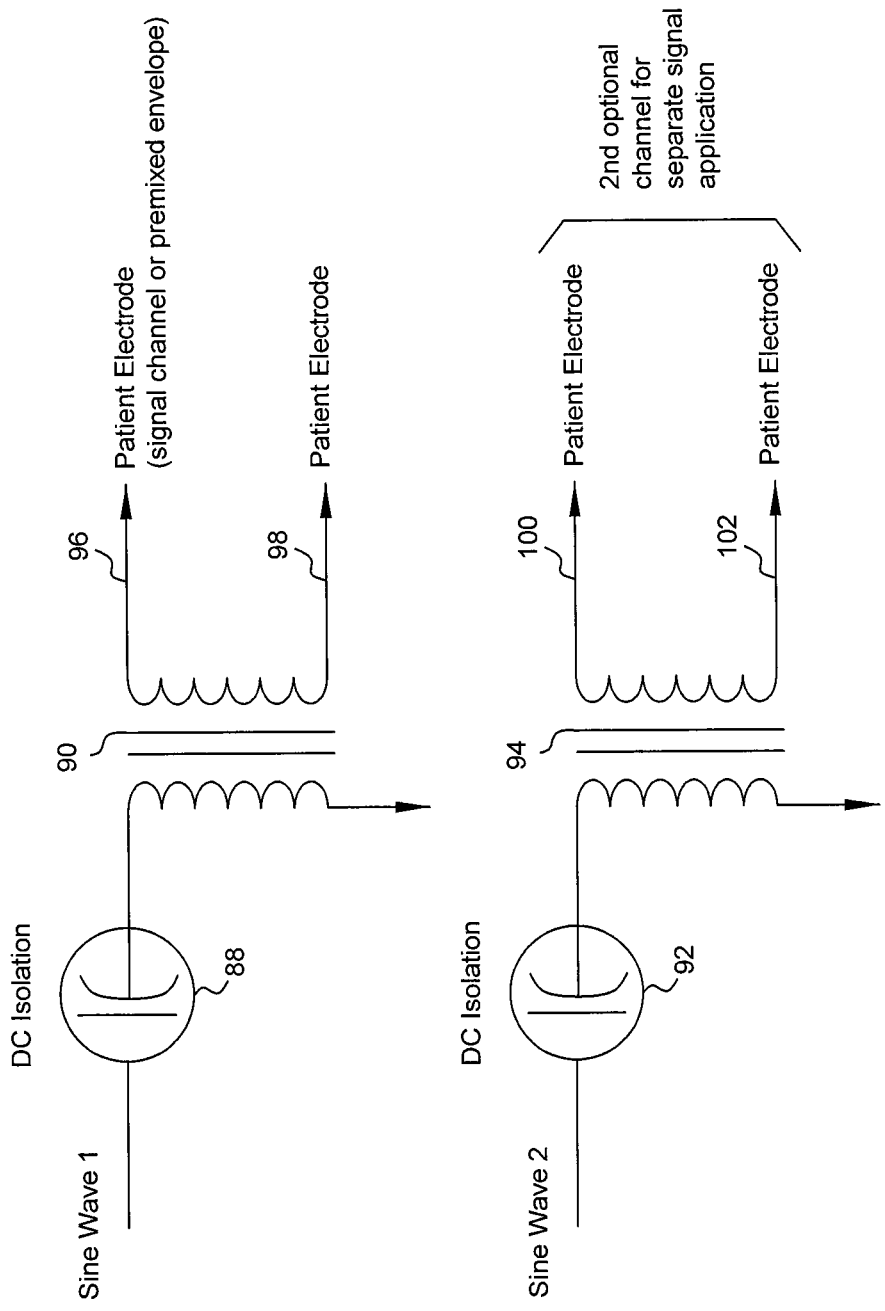
FIG. 4 illustrates the coupling of Sine wave 1 and Sine wave 2 to the electrodes when the apparatus is constructed around ground reference (local Apparatus ground) linear power amplifiers in accordance with some embodiments of the present disclosure.

FIG. 4 illustrates the coupling of Sine wave 1 and Sine wave 2 to the electrodes when the apparatus is constructed using around ground referenced (local Apparatus ground) linear power amplifiers in accordance with some embodiments of the present disclosure. The sine wave signal is coupled from the junction of current monitor 76 or 78 and voltage monitor 80 or 82 or 82 to a DC isolation capacitor 88 or 92. This capacitor removes any remaining DC component on the sine wave signal. The sine wave signal is coupled to transformer 90 or 94. The output of the transformer 90 is coupled to the patient electrodes. One output of each transformer 96 or 100 is coupled to a large signal electrode and the other to a small return electrode 98 or 102. The transformer provides voltage gain and patient/apparatus isolation. With bridged amplifiers or in Class D operation no such transformers are required unless additional voltage gain is needed. In various embodiments, the Dispersive electrode has a much larger surface area contacting the patient than the Pain Site electrode. This size ratio of the Dispersive electrode to the Pain Site electrode is at least 2:1. In some embodiments, the electrodes are the same size and act as both pain site and return electrodes for each other depending on the opposing delivery of the signals.

In some embodiments, a feedback network is disclosed. In various embodiments, the feedback network consists of two functional parts: 1) a circuit (Hardware), that monitors the patient-applied current and possibly voltage and 2) software that determines if the values measured require an output level change (Software). The parameter derived from the current and voltage is the impedance across the patient-applied electrodes. This parameter has been found by studies to be essentially invariant at a given frequency (frequency interval for this device) and over the range of applied potentials used clinically. Further, any impedance change due to a change in patient position essentially disappears when he or she either returns to the position held before the impedance change or after there is an equilibration of blood flow.

Figure 5:
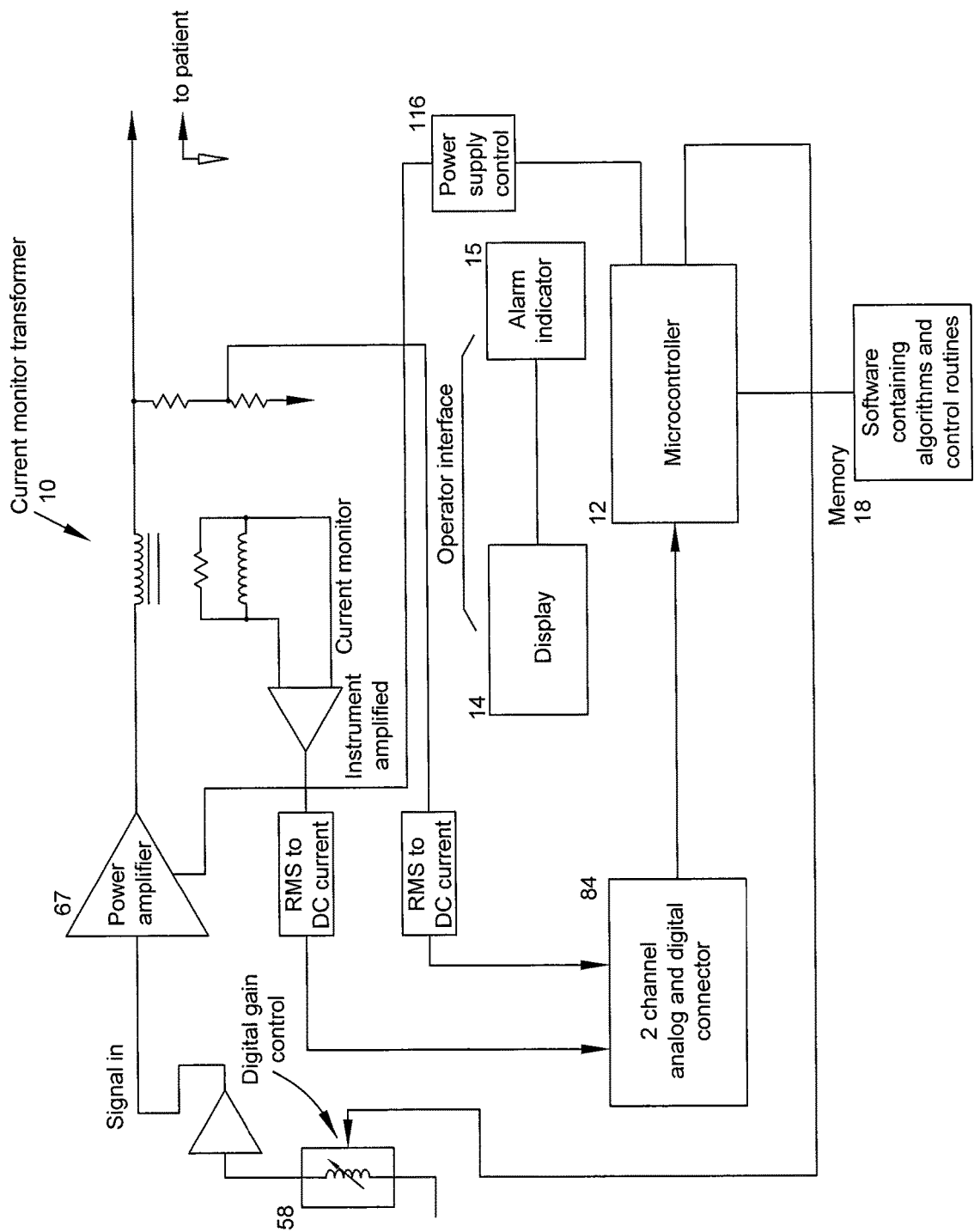
FIG. 5 illustrates the structure of an electrotherapeutic apparatus in accordance with some embodiments of the present disclosure.

FIG. 5 illustrates the structure of an electrotherapeutic apparatus according to some embodiments of the present disclosure. In various embodiments, a microcontroller 12 supervises the entire operation of the apparatus. The microcontroller 12 is responsible for interpreting operator commands and for displaying system status on the display panel 14. Additionally, the processor controls the frequencies of the signal sources, their levels and compensates for any variation in system load. This last function is important since changes in patient electric load can affect the signal level and the perceived sensation of the apparatus effect. The microcontroller 12 uses feedback to control signal levels by comparing the immediate electrical load to previously "learned" characteristic rules for a particular patient. The microcontroller 12 provides input to the digital gain control unit 58. Additionally, the microcontroller 12 receives operation instructions from software containing algorithms and control routines stored in memory 18. In various embodiments, memory 18 may be pre-programmed by an operator. The microcontroller 12 provides instructions to various portions of the signal generation system. The signal system generates two signals. In some embodiments, microcontroller 12 is also responsible for displaying alarms and indications via an indicator unit 15. In some embodiments, this includes an LED display unit having different colors. By way of example, the indicator unit 15 may display Green for indicating battery strength or charge level of the portable unit. Other parameters may identify Bluetooth capability, signal intensity, treatment time, and/or indicate errors or aid in troubleshooting. One of ordinary skill in the art will appreciate that the indicator unit 15 may display various visual indicators useful to a patient for displaying alarms and operations of the electrotherapeutic unit.

The microcontroller supervises the operation by adjusting the digital gain control 58 for the apparatus. As described above, the signals from above are buffered 60 and 62 and applied to a power gain stage. The power stage consists of one or more amplifiers 67, 69 capable of supplying a wide range of voltages into any physiological and electrode load over the frequency ranges used. The second class of amplifiers, which also improves performance in a portable system, is that of Class-D.

As described above, there are several ways of generating and amplifying signals. All methods rely on individual oscillators and amplifiers. Class $AB_1$ amplification is a well-known method for amplifying sinusoidal signals. In the present disclosure the input to these amplifiers are controlled-amplitude sinusoidal signals of differing frequencies. Regulation of the output signal, as a function of load impedance, is achieved by the close-looped feedback network which also can either alter the gain of the power amplifier or the amplitude of the power amplifier's input signal.

Another method uses Class D switching amplifiers. There are two ways these amplifiers can be used to generate the signals. In one method pulse width modulated signals, representing the two frequencies is generated by a microcontroller 12. The width of the pulses defines the amplitude of the final signals and the rate of the pulse packet defines the frequency. These pulse packets drive a set of field effect switching transistors. The output of these transistors is low-pass filtered, reconstructing the sinusoidal signal of the desired amplitude. The second method uses a comparator, connected to a reference sinusoidal signal of set amplitude and a triangular ramp signal. The output of the comparator is a pulse width modulated signal that drives the same circuit, as mentioned above, to generate the output signal. Regulation of the output signal can be achieved by a feedback loop from the output to a summing circuit at the input or monitoring the output using an analog-to-digital circuit on the system's microcontroller 12. The microcontroller 12 can use the digital values of the changes in the output signal, due to changes in load impedance, to adjust the pulse width modulation signal to compensate for these variations.

The unique third method is one derived from high-efficiency radio frequency amplifiers—Class E. Class E is a switching amplifier where a power MOS field effect transistor is driven by a square wave signal whose repetition rate corresponds to the desired output frequency. The amplified pulse is bandpass-filtered recreating an amplified sinusoidal signal. The amplitude of the signal is set by the power supply voltage level. Regulation of the output is achieved by sampling the output signal and using it to control the power supply voltage level to maintain fixed output signal amplitude independent of load impedance. The regulation circuit can be realized by direct hardware feedback or by using the microcontroller's 12 analog-to-digital converter to measure the output amplitude and using the difference between desired amplitude and actual amplitude to set the control voltage on the power supply.

Advantageously, the ability to regulate the output of a digital amplifier into a dynamic load makes for a much more comfortable smooth treatment sensation as the patient moves during treatment. This ultimately results in excellent patient compliance using the device. Regulation of the output signal can be achieved by a feedback loop from the output to a summing circuit at the input or monitoring the output using an analog-to-digital circuit on the system's microcontroller. The microcontroller can use the digital values of the changes in the output signal, due to changes in load impedance, to adjust the pulse width modulation signal to compensate for these variations.

Figure 6:
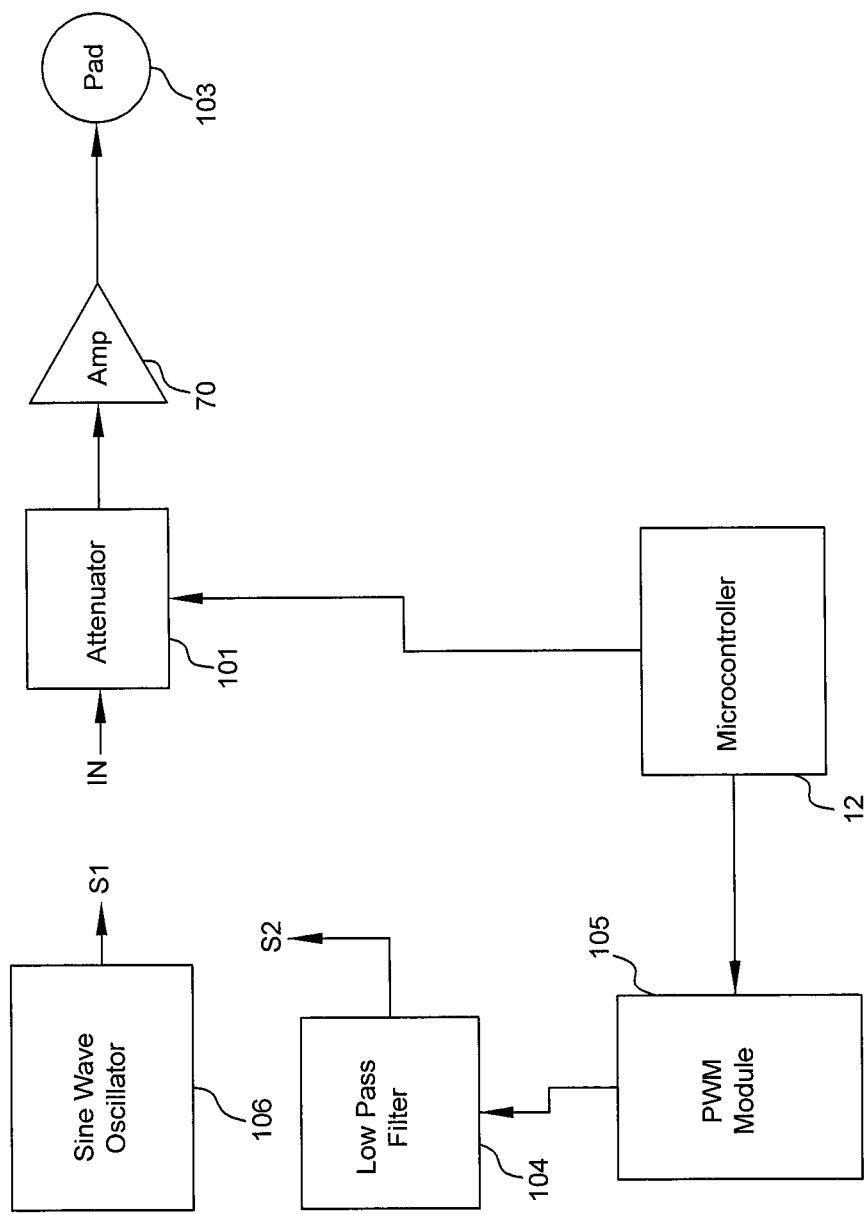
FIG. 6 illustrates the general block structure of an electrotherapeutic apparatus in accordance with some embodiments of the present disclosure.
Figure 7:
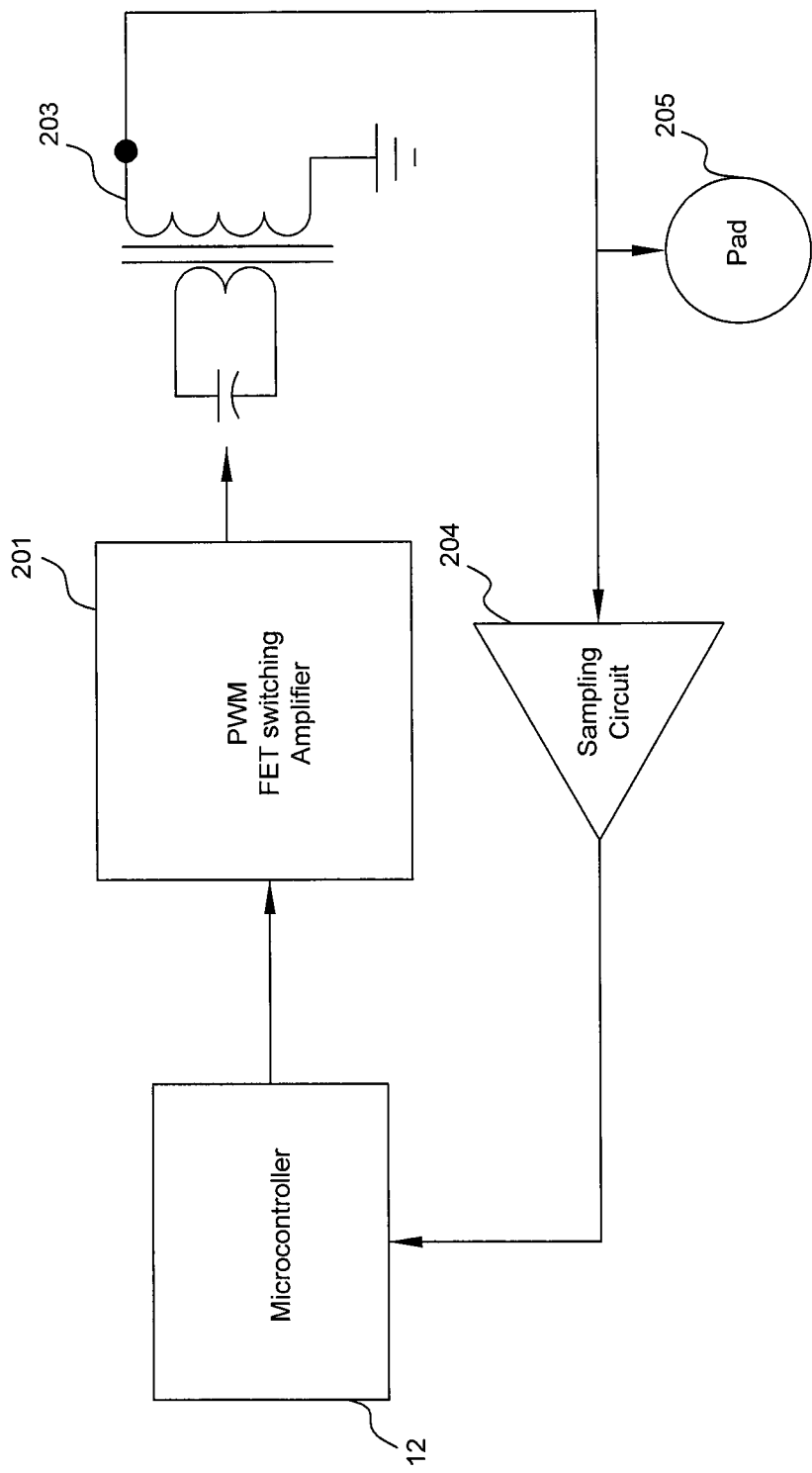
FIG. 7 illustrates the general block structure of an electrotherapeutic apparatus in accordance with some embodiments of the present disclosure.
Figure 8:
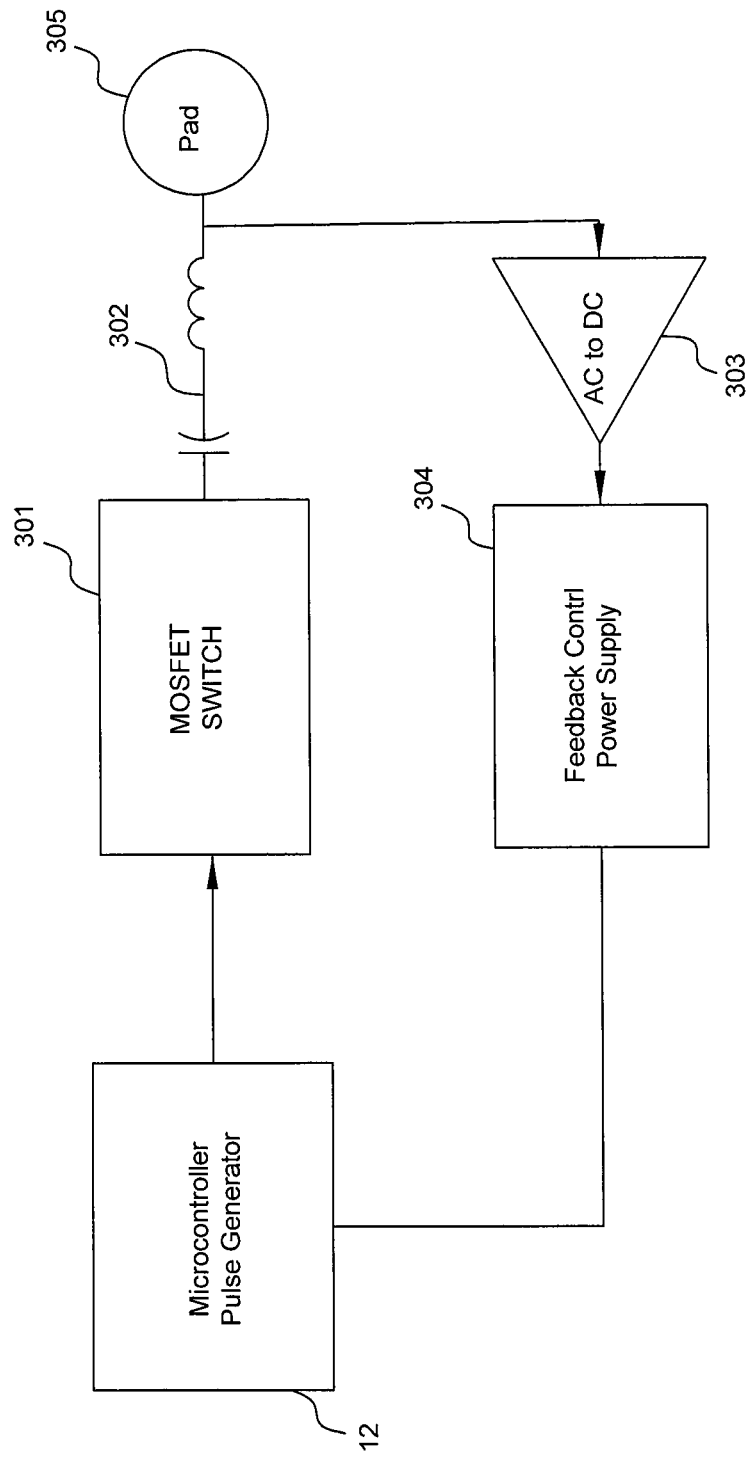
FIG. 8 illustrates the general block structure of an electrotherapeutic apparatus in accordance with some embodiments of the present disclosure.

FIGS. 6-8 illustrate the general block structures of an electrotherapeutic apparatus in accordance with some embodiments of the present disclosure. In FIG. 6, according to some embodiments, S1 represents a sine wave reference signal generated by an analog oscillator 106. S2 represents a sine wave reference signal which is derived from low-pass filtered 104 pulses generated by the pulse width modulation (PWM) 105 module within the microcontroller 12. These are two possible ways of producing the reference signals. Attenuator 101 controls the amplitude of the reference sine wave which is fed to a class AB power amplifier 70. The output of the power amplifier 70 is applied to the patient-connected electrode 103. According to some embodiments, each channel requires (either 106 or 104), 101, 70, 12 and 103.

In FIG. 7, according to various embodiments, microcontroller 12 generates a PWM signal where the relative widths of the pulses control the ultimate amplitude of the final signal. A MOSFET transistor bridge switching network 203 is driven by the PWM signal described above. The output of this bridge is a large-signal replica of the original PWM signal—Class D. This signal is passed to a low-pass filter 203 network with a cutoff frequency much lower than the pulse rate of the PWM signal. The transformer supplies voltage gain to enable the use of low voltage power supplies and low voltage monolithic or discrete device class D amplifiers. Two forms of feedback, for signal regulation, can be used: 1. A direct feedback network in the loop between the output of the switching MOSFETs to the input or 2. Using the microcontroller's 12 analog-to-digital converter to sample 204 the analog output voltage and correct this voltage by dynamically varying the PWM signal. Each channel requires 201, 203, 204 and 205.

In FIG. 8, according to various embodiments, a Class E embodiment is disclosed. Class E is a switching amplifier where 50% duty-cycle pulses drive a power switch. The pulse repetition rate is at the frequency of interest. Microcontroller 12 generates the logic-level pulses. This signal drives a MOSFET power 301 transistor whose output swings between the power supply rail and near ground. This output signal is applied to an inductor/capacitor network 302 resonant at the frequency of interest. This signal is applied to the patient-connected electrode 305. Output amplitude is entirely set by the power supply rail voltage 304. The output signal is sampled and converted to a DC correction voltage 303. This voltage is used to trim the power supply voltage thereby regulating the output signal. Each channel individually requires 301, 302, 303, 304 and 305.

Class E amplifiers are characterized by simple design, construction and relatively high efficiency (>=90%). Our therapeutic signal difference of around 122 Hz can be delivered over a band of frequencies ranging from around 1 KHz to 30 KHz. As the frequency rises the body-load impedance drops. Therefore, for a given delivered power a lower output voltage is required. Class E amplifiers require 2 amplifier channels each separately applied to one of the two electrodes. The second electrode acts as the return path for each signal. Class E amplifiers are pulse-switched tuned-output devices where the load impedance is matched to the tuned output network of the amplifier. The design of the amplifiers as disclosed according to some embodiments requires that each amplifier be tuned to some mid-band frequency (e.g.) 10 KHz and 10.122 KHz at the average body load impedance. The operational voltage is set by the amplifier' MOSFET drain voltage. If the patient load varies it will be reflected in the measured applied voltage and current. These voltages and currents are monitored by the system microcontroller 12. The contents of look-up tables, indexed by the desired voltage and expected current, are compared to the drain voltage and the measured voltage and current. The error in expected and measured voltage and current are used by an algorithm to determine what change in operating frequencies would be required to return the output signal to its proper power density. Since, as indicated above, we have a fairly broad available frequency range it should be possible to dynamically correct for the impedance mismatch and apply the proper power to the patient load.

Transformer

For both safety and economic reasons, it is desirous to operate the device's power amplifier section at lower output voltages. In terms of safety, the use of low voltage power amplifiers guarantees that a harmless D.C. voltage level would be applied to the patient if the D.C. isolation mechanism should fail. Additionally, the use of lower supply rails lessens the complexity and cost of the power amplifier's power supplies and greatly broadens the number and types of power amplifier topologies and/or devices that can be used. This allows for more choice in determining the best power amplifier for a given price and performance. In the device transformers can supply either D.C. isolation and/or voltage gain. In one embodiment, a high coupling toroidal transformer was used to increase the device output voltage by a factor of 2.4. This kept the power supply design simple and inserted a magnetic isolation barrier between the patient and the device. In another embodiment, as discussed in more detail below, an autotransformer configuration is used to boost the output voltage from 6 V RMS to 36 V RMS. However, the inherent losses and non-linear responses found with any transformer causes its output voltage to vary as a function of the load it is connected to. This failure-to-follow or poor regulation can and does lead to patient discomfort. In order to take advantage of a transformer's voltage gain it is necessary to compensate for poor regulation.

Poor regulation can be overcome via two methods: 1. Electronically—where a sample of the output controls the gain of the output circuitry; and 2. Utilizing the microcontroller 12—where a sample of the output is converted and used by the microcontroller 12 to determine a correction to the setting of the digital intensity control.

For the configuration where the transformer has isolated primary and secondary windings, the output is sampled and returned to the amplifier section through an isolation amplifier. This is required in order to maintain the D.C. isolation barrier created by the transformer. The output of the isolation amplifier is used to either vary the bias on a transconductance amplifier or the resistance of an attenuator which controls the gain of the device's preamplifiers or power amplifier directly, in response to deviations in the output signals relative to a reference. For the autotransformer configuration, no isolation amplifier is used since this transformer-type is inherently non-isolating. In this case capacitors are used to isolate the D.C. from the output. Regulation for this transformer output is maintained by connecting the transformer primary tap or an attenuated signal developed from the high voltage tap back to the inverting input of the power amplifier. This closes the amplifier loop thereby dynamically compensating for the transformer's non-ideal behavior.

Safe Operating Limits

Paramount to any medical electrical device is the prevention or discontinuation of device's operation when it encounters an unsafe condition. For the electrotherapy device we have developed, the major unsafe condition arises when the applied current causes a rise of skin temperature above 41° C. causing a thermal burn. Another condition, which is more unpleasant than dangerous, is when the output voltage abruptly changes as a function of load change. This is perceived by the patient as a surge-like feeling. This condition is normally not associated with an increase of skin current density and as such cannot cause injury.

There are two methods which have been used to ameliorate the burn-mode of device operation. One method uses the microcontroller 12 and its software to determine if the current flow exceeds a pre-programmed limit. The output current is sampled either by a small-valued series resistor or a resistor terminated current transformer. The analog level which represents the output current is converted to a digital value and compared continuously with the preset limit. When this limit is exceeded the software turns off the power amplifier(s) or their power supplies and signals the user to the over-current condition.

The second method of safe operational control also uses a measure of the output current or a measure of the load impedance as determined from this current and applied voltage. Current monitoring is affected as with the limit control above. Voltage monitoring is performed by sampling the output voltage and converting it to a digital representation of the RMS applied voltage. Software uses these values to determine if operation is exceeding safety guidelines. For example, a drop in load impedance increases the output current. Impedance values derived from low output-level startup current and voltage values are used to determine impedance measures. An algorithm sets the allowed current limits for a given output level. If device operation falls outside of these limits, for a predetermined period, the device can shut down the device or the ability to increase signal intensity can be disabled. The use of an operational-limit algorithm and time measure is critical since there can be situations (for example, output settling or momentary electrode condition changes) where operation falls outside certain limits but are not a reflection of a device failure or other unsafe condition. Further, dynamic lowering of the device output level is used when for a given intensity the impedance changes outside of predetermined limits for a given period. This mode of operation is used to lessen or eliminate the chance of a burn when the power density rises above guideline limits. The operator can still bring down the intensity and need not stop operation as long as the maximum allowed current is never exceeded. Normal device operation is restored when the measured impedance returns to within pre-determined operational limits. If this fails to happen within a predetermined elapsed time the device is disabled, and the condition is indicated to the operator.

Timer

According to various embodiments, a timer, which can be auto-loaded with a default treatment time or have the treatment time set by the operator, is initialized and maintained by the device's system software. This timer has several uses. It shuts off the device at the end the elapsed treatment time and it acts as a reference for the safe-operation-limits software to help determine whether a time-dependent excursion outside of normal impedance boundaries is interpreted as a failure or transient event. This could include limiting the number of treatments a patient can receive within a pre-determined period. The timer can also be used to change the device output intensity as a function of a pre-loaded time-sequenced treatment protocol. The amount of aggregate treatment time accumulated by the device is updated by the timer at the end of each treatment session. This information is used to determine when battery replacement or other service procedures should be performed.

Autotransformer

It is useful if the operating voltage of the output power amplifier could remain low. This lessens losses in the switching power supply that increase as the voltages needed rise. Additionally, higher voltage amplifiers are more expensive and usually physically larger. In various embodiments, one method to achieve voltage gain is by using a transformer. Typical transformers have a primary winding and a secondary winding. They offer voltage or current gain while isolating the input circuit from the output circuit. Unfortunately, there are losses associated with the core of the transformer, the winding resistance and imprecise coupling (magnetic) between the primary and secondary winding. One way to utilize the voltage gain capabilities of a transformer is through the use of the autotransformer configuration. Here the primary and secondary share the same winding. For voltage gain assume that the input signal, in closed feedback loop with the output amplifier, is applied to N turns of wire wrapped around a ferromagnetic core (ideally a toroid) the secondary winding is just a continuation of the primary winding (electrically the same wire). To get twice the voltage from the secondary the winding is continued for another N turns on the same core. The output is taken from the end of the secondary winding. In this configuration there is tighter magnetic coupling and good output regulation (as opposed to what is found with isolated primary and secondary windings). Additionally, the autotransformer is cheaper, electrically better and smaller than a normal transformer. If desired, the output at the secondary can be attenuated and if need be phase-shifted and used to close the loop of the power amplifier. The attenuation is necessary to maintain the amplifier's differential input voltages close in value as the feedback loop requires.

Construction

Figure 9:
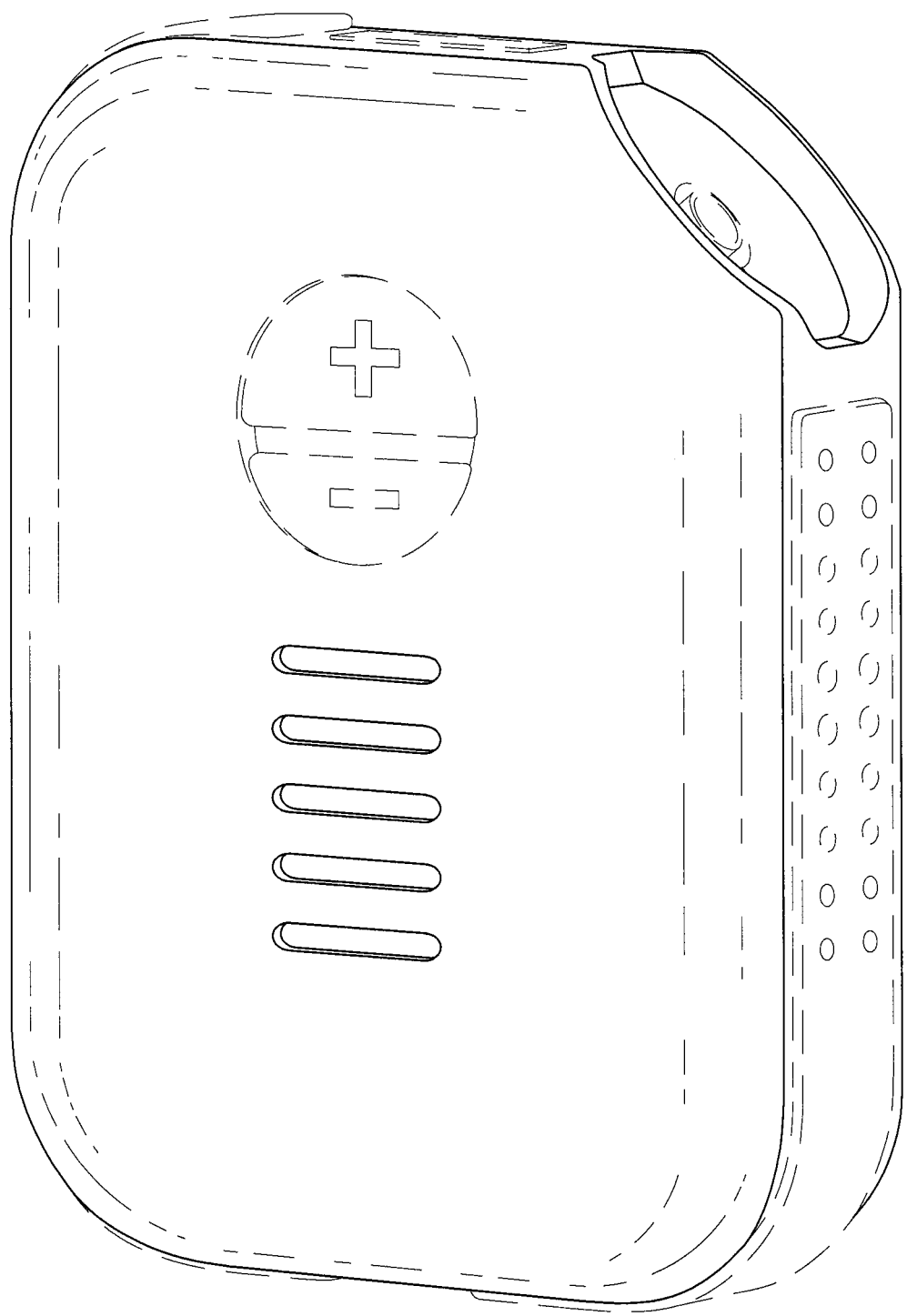
FIG. 9 is a depiction of an electrotherapeutic device in accordance with some embodiments of the present disclosure.

FIG. 9 is a depiction of an electrotherapeutic device according to some embodiments of the present disclosure. According to various embodiments, the electrotherapy device includes an option for physically manipulating the intensity of the treatment. In some embodiments, the electrotherapy device includes a communications unit for communicating with a client device to adjust the parameters remotely. For example, the electrotherapy device may be operated remotely using a client device connected via Bluetooth or WiFi communications. It should be appreciated to one of ordinary skill in the art that a client device may remotely connect to the electrotherapy device in various ways for operation. In some embodiments, the electrotherapy device may include an angled female port for connecting the electrodes. The angled port advantageously permits ease of access and wearable functionality for the electrotherapy device. In various embodiments, the angled port includes a depression for recessing the connection of the electrodes. In some embodiments, the recessed port includes a plurality of indentations configured to receive a cable attached to the male connector such that the cable is located against the side edges of the substantially rectangular device when the male connector is inserted into the female port It may be emphasized that the above-described embodiments, are merely possible examples of implementations, and merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claims.

Embodiments of the subject matter and the functional operations described in this specification may be implemented in electrical or electromechanical means, including the structures disclosed in this specification and their structural equivalents, or in combinations of one or more of them. Embodiments of the subject matter described in this specification may be implemented as an electrical or electromechanical unit.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments may also be implemented in combination in a single embodiment. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

While various embodiments have been described, it is to be understood that the embodiments described are illustrative only and that the scope of the subject matter is to be accorded a full range of equivalents, many variations and modifications naturally occurring to those of skill in the art from a perusal hereof

What is claimed is:

1. A method for providing therapeutic electric current to a treatment site of a patient comprising the steps of:
generating a first and second signal having a frequency difference between 1 Hz and 300 Hz, wherein each signal has a frequency of at least 1 KHz and are amplified by Class D switching amplifiers;
minimizing the DC component of the first and second signals using balanced amplifiers;
operatively coupling a first electrode of at least one pair of electrodes to a patient's body on or beneath a first epidermal or mucous membrane surface;
operatively coupling a second electrode of at least one pair of electrodes to a patient's body on or beneath a second epidermal or mucous membrane surface;
forming a therapeutic signal configured to reduce pain at a treatment site by simultaneously sending a first signal from the first electrode to the second electrode and sending a second signal from a second electrode to the first electrode, and then simultaneously sending the first signal from the second electrode back to the first electrode and the second signal from the first electrode back to the second electrode, wherein the first and second signals are linearly independent off phase alternating current signals; and adjusting the therapeutic signal utilizing a feedback system based on impedance changes within the patient's body.

2. The method of claim 1, wherein the first and second signals are summed before being amplified.

3. The method of claim 1, wherein the therapeutic signal is a linear combination of said first and second signals.

4. The method of claim 3, wherein the therapeutic signal is a sum of said first and second signals.

5. The method of claim 1, wherein the feedback system is configured to monitor at least one of a voltage or a current associated with the impedance of a patient's body and control the therapeutic signal in response.

6. The method of claim 1, wherein the therapeutic signal is controlled so as to maintain a monitored voltage at a constant voltage level.

7. The method of claim 5, wherein the feedback system utilizes software configured to determine whether a change in the therapeutic signal is required, based at least in part on at least one of said voltage and current.

8. The method of claim 1, wherein the base frequency value of the two signals is between 200 Hz and 500 KHz.

9. The method of claim 1, wherein the feedback system comprises:
a resistor or current transformer that monitors a current through the patient;
an amplifier for differentially detecting a voltage developed by said current passing through the resistor;
a gain block for further amplifying the detected voltage;
a buffered attenuator for sampling the voltage across the two electrodes and setting the voltage's value to within a predetermined range of an analog-to-digital (ADC) circuit to which the voltage is to be input;
an analog multiplexer having as a first input thereto an output of the gain block and having as a second input thereto an output of the buffered attenuator, the analog multiplexer configured to selectively output either the first input or the second input, based on a signal from a CPU;
a RMS to DC converter having input thereto for an output of the analog multiplexer, and being configured to output a DC level approximately equal to the RMS value of the applied signal;
an analog-to-digital converter configured to convert an analog output of the RMS to DC converter into a digital signal; and
a digital attenuator configured to change said output level, as required by the feedback system.

10. The method of claim 1, further comprising the steps of:
monitoring via a timer, the treatment time set by the operator when the electrotherapy device is initialized.

11. A method for providing therapeutic electric current to a treatment site of a patient comprising the steps of:
generating a first and second signal having a frequency difference between 1 Hz and 300 Hz, wherein the first and second signal are two sinusoidal alternating current signals having a base frequency value of between 200 Hz and 500 KHz which are amplified by Class D switching amplifiers;

coupling a first electrode of at least one pair of electrodes to a patient's body on or beneath a first epidermal or mucous membrane surface;

coupling a second electrode of at least one pair of electrodes to a patient's body on or beneath a second epidermal or mucous membrane surface; and forming a therapeutic signal configured to reduce pain at a treatment site by simultaneously sending a first signal from the first electrode to the second electrode and sending a second signal from a second electrode to the first electrode, and then simultaneously sending the first signal from the second electrode back to the first electrode and the second signal from the first electrode back to the second electrode, wherein the first and second signals are linearly independent off phase alternating current signals.

12. The method of claim 11, further comprising the steps of:
adjusting the therapeutic signal utilizing a feedback system based on impedance changes within the patient's body.

13. The method of claim 11, wherein the first and second signals are summed before being amplified.

14. The method of claim 11, wherein the therapeutic signal is a linear combination of said first and second signals.

15. The method of claim 14, wherein the therapeutic signal is a sum of said first and second signals.

16. The method of claim 12, wherein the feedback system is configured to monitor at least one of a voltage or a current associated with the impedance of a patient's body and control the therapeutic signal in response.

17. The method of claim 16, wherein the therapeutic signal is controlled so as to maintain a monitored voltage at a constant voltage level.

18. The method of claim 17, wherein the feedback system utilizes software configured to determine whether a change in the therapeutic signal is required, based at least in part on at least one of said voltage and current.

19. The method of claim 18, wherein the feedback system comprises:
a resistor or current transformer that monitors a current through the patient;
an amplifier for differentially detecting a voltage developed by said current passing through the resistor;
a gain block for further amplifying the detected voltage;
a buffered attenuator for sampling the voltage across the two electrodes and setting the voltage's value to within a predetermined range of an analog-to-digital (ADC) circuit to which the voltage is to be input;
an analog multiplexer having as a first input thereto an output of the gain block and having as a second input thereto an output of buffered attenuator, the analog multiplexer configured to selectively output either the first input or the second input, based on a signal from a CPU;
an RMS to DC converter having input thereto an output of the analog multiplexer, and being configured to output a DC level approximately equal to the RMS value of the applied signal;
an analog-to-digital converter configured to convert an analog output of the RMS to DC converter into a digital signal; and
a digital attenuator configured to change said output level, as required by the feedback system.

20. An electro therapy and neurostimulation device comprising:

a substantially rectangular shape having at least one corner of the outer peripheral edge of the device at an angle, and a depression disposed within the angled portion of the device;

a female port disposed within the depression configured to receive a male connector; and wherein the depression comprises a plurality of indentations configured to receive a cable attached to the male connector such that the cable is located against the side edges of the substantially rectangular device when the male connector is inserted into the female port.

* * * * *